(12) United States Patent
O'Brien et al.

(10) Patent No.: US 7,662,217 B2
(45) Date of Patent: Feb. 16, 2010

(54) SOIL SEPARATOR AND SAMPLER AND METHOD OF SAMPLING

(75) Inventors: Barry H. O'Brien, Idaho Falls, ID (US); Paul D. Ritter, Idaho Falls, ID (US)

(73) Assignee: Battelle Energy Alliance, LLC, Idaho Falls, ID (US)

(*) Notice: Subject to any disclaimer, the term of this patent is extended or adjusted under 35 U.S.C. 154(b) by 371 days.

(21) Appl. No.: 11/695,650

(22) Filed: Apr. 3, 2007

(65) Prior Publication Data

US 2008/0245706 A1 Oct. 9, 2008

(51) Int. Cl.
*B01D 46/38* (2006.01)

(52) U.S. Cl. .............................. 95/275; 55/474; 95/273; 95/274; 96/413

(58) Field of Classification Search ................... 55/474; 95/267, 268, 273, 274, 275; 96/397, 413
See application file for complete search history.

(56) References Cited

U.S. PATENT DOCUMENTS

| | | | | |
|---|---|---|---|---|
| 2,689,973 A * | 9/1954 | Lee et al. ..................... 264/117 |
| 2,829,955 A * | 4/1958 | Goedkoop .................. 422/141 |
| 3,370,938 A * | 2/1968 | Newman et al. ............. 423/110 |
| 3,631,608 A * | 1/1972 | Maresca et al. ............... 34/364 |
| 3,915,657 A * | 10/1975 | Staffin et al. ................ 422/143 |
| 4,302,370 A | 11/1981 | Buse |
| 4,591,103 A | 5/1986 | Andrews et al. |
| 4,754,655 A | 7/1988 | Parker, III et al. |
| 4,820,315 A | 4/1989 | DeMarco |
| 5,034,196 A * | 7/1991 | Zenz et al. ................... 422/142 |
| 5,052,756 A | 10/1991 | Wada et al. |
| 5,323,930 A * | 6/1994 | Masclet et al. ................ 222/71 |
| 5,330,657 A * | 7/1994 | Chapman et al. ............ 210/712 |
| 5,421,527 A | 6/1995 | Corte |
| 5,589,073 A * | 12/1996 | Chapman et al. ............ 210/704 |
| 5,599,137 A | 2/1997 | Stephenson et al. |
| 5,779,989 A * | 7/1998 | Tomasicchio et al. ....... 422/145 |
| 5,879,638 A * | 3/1999 | Tomasicchio ................ 422/143 |
| 6,082,548 A * | 7/2000 | Stephenson et al. ............ 209/4 |
| 6,183,169 B1 * | 2/2001 | Zhu et al. .................... 406/123 |
| 6,341,567 B1 * | 1/2002 | Robertson et al. ........... 110/203 |
| 6,684,917 B2 | 2/2004 | Zhu et al. |
| 7,309,383 B2 * | 12/2007 | Beech et al. .................. 95/268 |
| 7,390,339 B1 * | 6/2008 | Warrick et al. ................ 55/346 |
| 7,569,093 B2 * | 8/2009 | Pranda et al. .................. 95/23 |
| 2009/0169435 A1 * | 7/2009 | Kominsky et al. ........... 422/104 |

\* cited by examiner

*Primary Examiner*—Duane Smith
*Assistant Examiner*—Sonji Turner
(74) *Attorney, Agent, or Firm*—TraskBritt

(57) ABSTRACT

A soil sampler includes a fluidized bed for receiving a soil sample. The fluidized bed may be in communication with a vacuum for drawing air through the fluidized bed and suspending particulate matter of the soil sample in the air. In a method of sampling, the air may be drawn across a filter, separating the particulate matter. Optionally, a baffle or a cyclone may be included within the fluidized bed for disentrainment, or dedusting, so only the finest particulate matter, including asbestos, will be trapped on the filter. The filter may be removable, and may be tested to determine the content of asbestos and other hazardous particulate matter in the soil sample.

10 Claims, 3 Drawing Sheets

SOIL SEPARATOR AND SAMPLER AND METHOD OF SAMPLING

GOVERNMENT RIGHTS

This invention was made with government support under Contract No. DE-AC07-05-ID14517 awarded by the U.S. Department of Energy. The government has certain rights in the invention.

BACKGROUND OF THE INVENTION

1. Field of the Invention

The present invention relates to soil samplers for use in determining materials in soil, more particularly the presence of extremely fine particulates, such as asbestos. The present invention is also directed to methods of testing a soil for asbestos content.

2. State of the Art

Asbestos exposure has been linked with various diseases, including lung cancer. Asbestos may be present naturally in soil, however, with mining operations, soil having higher asbestos concentrations may be exposed to the air. Particularly in dry, windy conditions, asbestos exposure is a concern for nearby residents. Cleanup for such a site can be expensive, as the quantity of soil needing removal and/or remediation may be immense. It is necessary to identify sites with asbestos contamination, as well as to identify the sites with the highest level of asbestos concentration.

Soil specimens may be taken quite readily; however, the samples must be tested to determine the level of asbestos content. It may be less cost-prohibitive to extract the asbestos from a soil sample on-site. The asbestos that has been extracted may then be transported and tested in a laboratory facility, rather than transporting the entire soil sample to a testing facility. One conventional method of extracting asbestos from the soil utilizes a glovebox. The soil sample may be gathered in a jar, then the jar may be placed in the glovebox. The glovebox may have a main chamber for handling and manipulating hazardous materials, and gloves, which may be accessed from an exterior of the glovebox, to enable a user to reach into the box and work with the hazardous materials inside, while being separated from the hazardous materials by the gloves. The jar containing the soil sample may be agitated and shaken by a user, and then an air sample may be taken from a headspace of the jar to be analyzed for asbestos.

However, conventional sample collection methods using a glovebox are time intensive, requiring manual manipulation of the soil sample and manual collection of the sampled air. In addition, the test results may be inaccurate due to reliance upon manual agitation of the soil sample. Further, the recovery fraction of asbestos may be too small to provide accurate test results.

Therefore, it would be advantageous to provide a method and a device for collecting an asbestos sample from a soil specimen that requires less manpower, less time, and provides a greater recovery fraction of asbestos.

BRIEF SUMMARY OF THE INVENTION

One embodiment of the present invention includes a method of separating particulate matter from a soil sample. The method comprises introducing the soil sample to a container, applying a vacuum to the container, fluidizing a plurality of particulates of the soil sample within the container, drawing fluidizing air from the container across a collection filter, and collecting the fluidized particulate matter on the collection filter. The soil sample may be introduced to a funnel-shaped container, also known as a spouted fluidized bed or a cylindrical container, also known as a cylindrical fluidized bed. A portion of the fluidized plurality of particulates may be disentrained and remain within the container rather than being drawn across the collection filter. The largest particulates, particularly the dust, may be disentrained. A cyclone or a baffle may be provided in the container or in the gas outlet from the container to enhance disentrainment. The vacuum may be a high-efficiency particulate-arresting (HEPA) vacuum, and the fluidizing air may be exhausted through a HEPA filter, protecting personnel from exposure to hazardous particulates, particularly asbestos, that may escape capture, remaining suspended in the fluidizing air beyond the collection filter.

In an alternative embodiment, the method and apparatus may be used to sample asbestos content of the soil without fluidizing the soil sample. For example, air may be passed through the soil sample without fluidizing the sample. Alternatively, air may be flowed through an inlet to the container above the soil sample to allow sampling the air above the soil sample in the container.

Another embodiment of the present invention provides a soil separator system comprising a fluidized bed configured for receiving a soil sample therein, a removable collection filter in communication with the fluidized bed, and a HEPA vacuum system in communication with the removable collection filter. A vacuum line may extend between the collection filter and the vacuum system, and a flow meter and a regulator controlled by the flow meter may be in fluid communication with the vacuum line.

The fluidized bed may comprise a spouted fluidized bed or cylindrical fluidized bed, and may include a baffle, a cyclone, or both such components, configured for disentrainment and disposed therein. A distributor, for example, glass frit, a TEFLON® plug with one or more holes, metal plate with one or more holes, or other porous materials, may be in fluid communication with an inlet of the fluidized bed to distribute the air therein. Optionally, a final HEPA filter may be in communication with a single HEPA vacuum to filter the exhaust air from the soil separator system for safety.

The soil separator system may be used to simultaneously test multiple soil samples. A plurality of fluidized beds, each configured for receiving a soil sample therein, may be in communication with a removable collection filter. The plurality of fluidized beds may be in communication with the single HEPA vacuum through a manifold.

Yet another embodiment of the present invention is a disposable fluidized bed comprising a container having a removable lid and configured for receiving and fluidizing a soil sample therein, an inlet at a first end of the container, an inlet cap for removably covering the inlet, an outlet at a second, opposing end of the container, and an outlet cap for removably covering the outlet. The container may include a tapered portion and a cylindrical portion. A baffle, a cyclone, or both such components, may be positioned within the container, in an inlet or in an outlet, and configured for disentrainment of a portion of suspended particulates therein. A distributor may be in communication with the inlet and configured for distributing the air within the disposable fluidized bed.

Other features and advantages of the present invention will become apparent to those of skill in the art through consideration of the ensuing description, the accompanying drawings, and the appended claims.

BRIEF DESCRIPTION OF THE DRAWINGS

The foregoing and other advantages of the invention will become apparent upon reading the following detailed description and upon reference to the drawings in which.

DETAILED DESCRIPTION OF THE INVENTION

Figure 1:
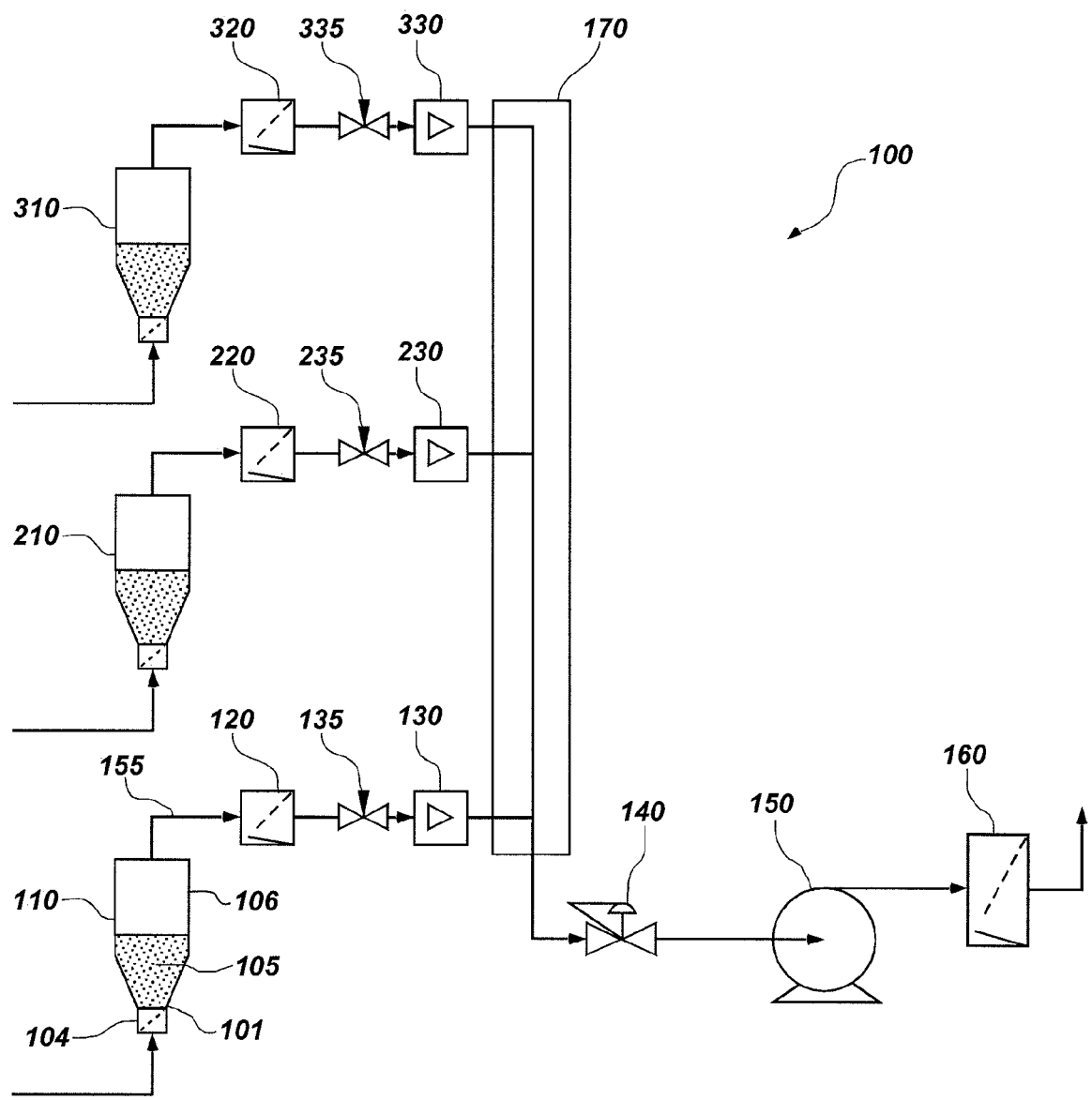
FIG. 1 shows a soil separator system of the present invention.

A flow diagram of a soil separator system 100 of the present invention is depicted in FIG. 1. The soil separator system 100 may be employed in a minimally equipped field laboratory to separate asbestos or other materials from a soil sample, or may be employed in a more completely equipped production laboratory environment, after transportation of an intact soil sample. The soil separator system 100 may include a fluidized bed 110 configured to fluidize a soil sample 105 therein. A vacuum pump or system 150 may be used to draw air through the fluidized bed 110. The air may enter the fluidized bed 110 at an inlet 101, and a distributor 104 positioned adjacent the inlet 101 is configured to distribute the air and retain the soil sample 105 within the fluidized bed 110. The soil sample 105 may be mixed and fluidized within the fluidized bed 110. Fluidization may suspend particulates, including asbestos particulates, in the air. The air and the suspended particulates may be drawn through a collection filter 120, where the suspended particulates may collect, via vacuum line 155. The collection filter 120 may be attached to the soil separator system 100 with a filter holder, so as to be removable for testing. A flow meter 130 may be in communication with a regulator 135 to control suction applied to the fluidized bed 110.

The soil separator system 100 may include a single fluidized bed 110, or may include a plurality of fluidized beds 110, 210, 310 (the number of depicted fluidized beds being non-limiting and by way of example only) in communication with a single vacuum pump or system 150. Each fluidized bed 110, 210, 310 may have an associated filter 120, 220, 320 and an associated flow meter 130, 230, 330 and regulator 135, 235, 335. A manifold 170 may be used to connect the plurality of fluidized beds 110, 210, 310 with the vacuum pump or system 150. The manifold 170 may include valves for controlling the air flow from the plurality of fluidized beds 110, 210, 310, or the flow may be controlled with the flow meters 130, 230, 330 and regulators 135, 235, 335.

A main vacuum regulator 140 may control the flow of air through the soil separator system 100. The vacuum pump or system 150 may drive the flow, and may be a high-efficiency particulate-arresting (HEPA) vacuum pump or system, with all air flow exiting the soil separator system 100 passing through a final filter 160, preferably a HEPA filter, prior to exiting the soil separator system 100. The final filter 160 may provide additional protection to personnel from exposure to any asbestos or other harmful particulate matter passing through the collection filter 120. The vacuum pump or system 150 may draw air through the soil separator system 100 for a designated processing time to enable thorough contact of air flow and the soil sample 105, and collection of asbestos on the collection filter 120. After a designated processing time has passed, the vacuum pump or system 150 may be turned off, the collection filter 120 may be removed for analysis, and a container 106 of fluidized bed 110 may be disconnected from the vacuum line 155 (see FIG. 2). A cap (not shown) may be placed over an outlet 109 and the inlet 101 of container 106, and the container 106, with the soil sample 105, may be disposed of, without any further personnel exposure to any potentially harmful material contained within. Such caps may include a valve, a U-trap, a stopper, a screw-on cap, friction-fit cap, and the like. A U-trap or valve may be placed over the inlet 101 of container 106 to contain the sample during operation.

Figure 2:
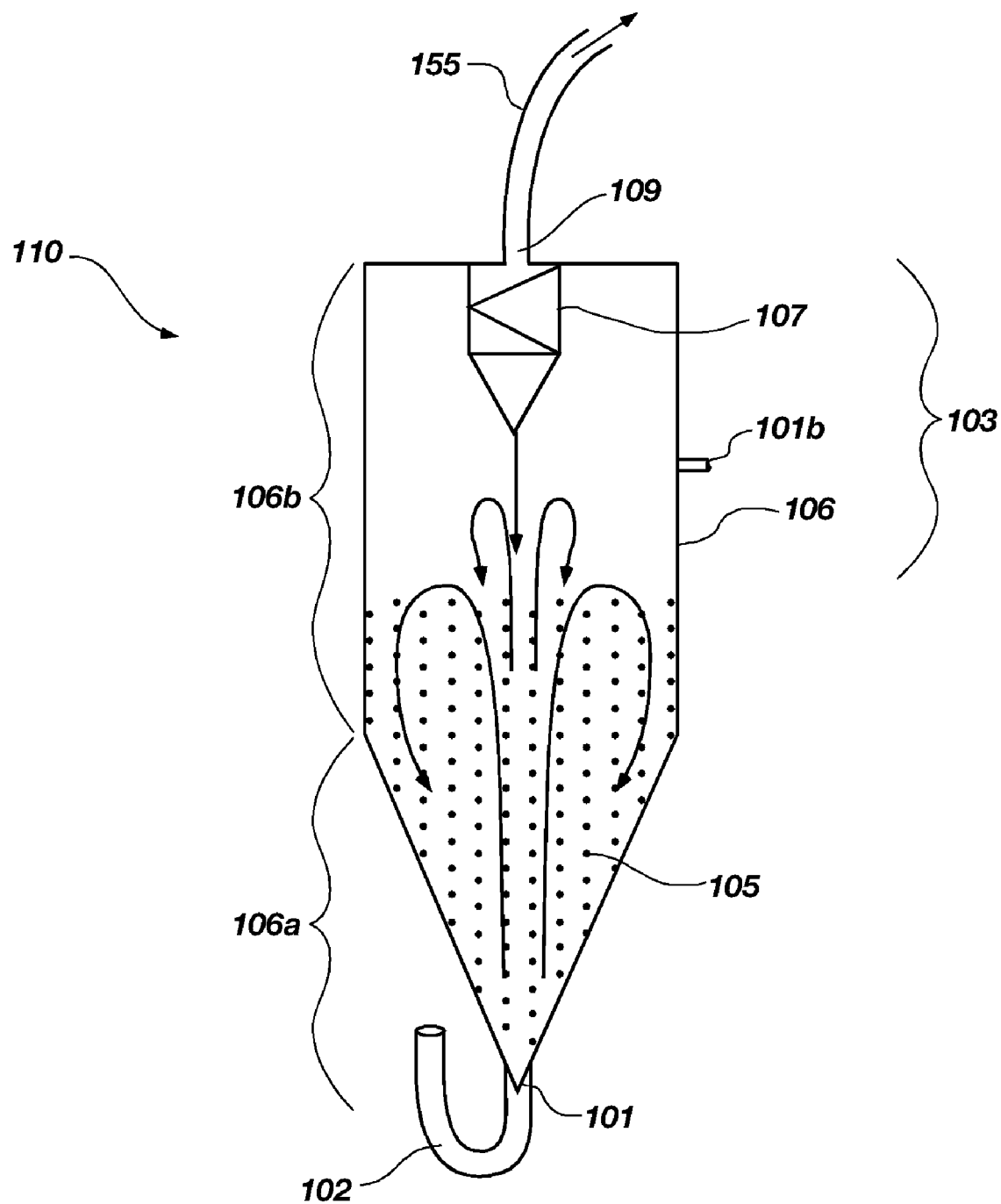
FIG. 2 shows a fluidized bed of the present invention.

One embodiment of a fluidized bed 110 of the present invention is depicted in FIG. 2. The fluidized bed 110 may comprise a funnel-shaped container 106, with a tapered portion 106a proximate the inlet 101 of the container 106 and an upper portion 106b, which may be cylindrical in shape. Optionally, the container 106 may have other configurations, for example, the container 106 may be cylindrical or box-like. A fluidized bed 110 having a funnel-shaped container 106, also known as a spouted fluidized bed, may be used to fluidize a large range of particle sizes with minimal air flow, in comparison to the air flow required by fluidized beds having containers of other shapes. The entire soil sample 105 may be circulated through a fluidizing zone within the container 106.

A distributor 104 may be disposed in the tapered portion 106a of the container 106, adjacent the inlet 101 of the container 106. A distributor may comprise a distributor plate, porous media such as a glass frit, or the like. The distributor is selected to allow a sufficient air flow rate into container 106 to fluidize the media without causing excessive pressure drop. A distributor plate may be, for example, a TEFLON® plug or metal disk with a hole. In one embodiment, the hole is approximately a 10 mm hole. Alternatively, the distributor plate may be a TEFLON® plug or metal disk with one or more smaller holes. The distributor may also be porous media such as glass frit or Dynapore™ fluidizing media. Optionally, the distributor 104 may be disposed outside the container 106, and air being drawn into the inlet 101 of the container 106 will first pass through the distributor 104, as shown in FIG. 1. The porous media may comprise, for example, glass frit having a pore size of about 150 to 220 microns and capable of allowing the air flow rate into container 106 required for fluidizing the sample without having excessive pressure drop. The distributor 104 may be used to distribute the air being drawn into the container 106 and to retain the sample in container 106. A U-trap (not shown) may be added to the inlet to container 106 to prevent solids from falling out of the vessel before air flow is started.

The soil sample 105 may be collected in the container 106, or the soil sample 105 may be collected in conventional containers, and transferred to the container 106 of the present invention. Optionally, collecting the soil sample 105 directly in the container 106 of the present invention may minimize personnel exposure to hazardous materials. The inlet 101 of container 106 may have a cap to contain the soil sample 105. The cap may be removable and a distributor 104 may be attached to the cap of inlet 101. The inlet 101 may comprise one opening, or a plurality of openings, at one end of the container 106. The openings may be sized to enable air flow into the container 106 and retain the soil sample 105. Optionally, the inlet 101 may have a mesh covering, a U-trap, or a valve, holding the soil sample 105 in place and providing an inlet for outside air. The container 106 may be disposable after the soil sample 105 has been fluidized and the asbestos extracted. Such disposable containers 106 may be, for example, plastic, glass, or aluminum.

Outside air may be drawn in through the inlet 101 of the container 106 and into container 106 by suctioning from an outlet 109 of the container 106. The moving air may be used to fluidize the soil sample 105 in the fluidized bed 110, as shown in FIG. 2. Fluidization may include suspending particulates in an upward-flowing gas, for example, air, to form a gas-solid suspension. Vessels in which this suspension occurs are called fluidized beds because the suspended particles in the upward flowing gas behave like a fluid. The velocity of the gas may determine a size of the particle that is transported with the gas out of the container 106. At higher velocities, larger particulate matter may be transported from the container 106. In one embodiment, asbestos fibers that are about 0.5 to about 20 microns long and about 0.5 to about 2 microns in diameter are captured on the collection filter.

A disentrainment portion 103 (see FIG. 2) of the container 106 may be a portion of the fluidized bed 110 that provides an airspace above the soil sample 105. The disentrainment portion 103 may minimize dust carry-over to the collection filter 120 (FIG. 1). The heaviest particulates may drop from the air to the bottom of the container 106, while the finest particulate matter, including any asbestos, will remain suspended and pass to the collection filter 120. A cyclone 107 may be provided within the container 106 to dedust the air. The cyclone 107 is also known as a cyclone precipitator or a centrifugal separator. The cyclone 107 may be used to direct the fluidized air in a circular flow, and the largest particulate matter may drop from the circulating fluidized air back to the container 106. The asbestos and the smallest particulate matter will remain fluidized, and continue with the flow of air through the outlet 109 of the container 106 to the vacuum line 155 leading to the collection filter 120. The vacuum line 155 may comprise, by way of example, plastic, rubber, glass, or metal tubing. The tubing may be flexible or rigid. Additional vacuum lines may lead from the collection filter 120 to the regulator 135, the flow meter 130, the vacuum regulator 140, the vacuum pump or system 150, and the final filter 160.

In certain embodiments, the container 106 may include second inlet 101b located above the level of the soil sample. Second inlet 101b allows air to be drawn in to sample the air above the soil sample 105 without flowing air through the sample. In such embodiments, the air above the soil sample 105 may be filtered to collect airborne particles without disturbing or fluidizing the soil sample 105. The purpose of this option is to reduce the amount of asbestos entrained and collected on the collection filter 120 to stimulate asbestos release from low soil disturbance.

In other embodiments, an air flow rate less than that required to fluidize the soil sample 105 may be flowed through either inlet 101, 101b. Such lower flow rate may be used such that the bed is not fluidized and less particulate matter is entrained and collected on the collection filter 120. The purpose of this option is to reduce the amount of asbestos entrained and collected on the collection filter 120 to stimulate asbestos release from moderate soil disturbance.

Figure 3:
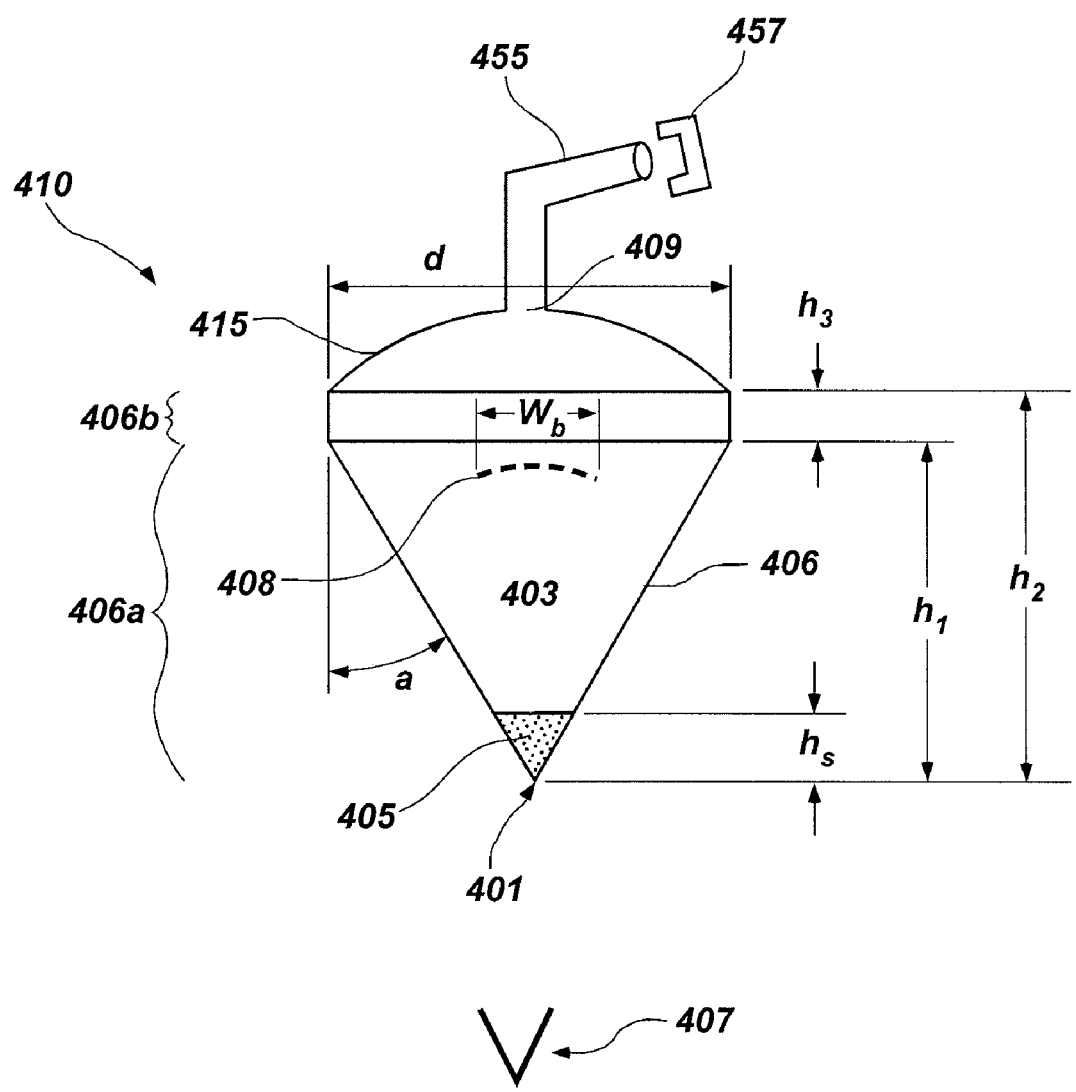
FIG. 3 shows another embodiment of a fluidized bed of the present invention.

FIG. 3 depicts another embodiment of a fluidized bed 410 of the present invention, having a container 406. The fluidized bed 410 additionally includes a baffle 408 (shown in dashed lines) to separate dust particles and asbestos, enabling the asbestos to pass through an outlet 409 of container 406 to the collection filter 120 as shown in FIG. 1, and minimize the dust collected on the collection filter 120. The baffle 408 may be of such a width $W_b$ and may be positioned so as to disturb the flow of air within the container 406, enabling the largest particulates to drop into the container 406, as the asbestos and other smaller particulates may continue with the flow of air, through the outlet 409 of the container 406. The container 406 includes a tapered portion, such as substantially conical, lower portion 406*a*. Each wall of the tapered lower portion 406*a* may extend off from vertical at an angle a. The angle a may be, for example, 30°, such that the bottom of the container 406 defines an included angle of 60°. The height $h_1$ of the tapered lower portion 406*a* may be, for example, between about 15 cm and about 20 cm, with about 17.1 cm being a currently preferred height. The overall height $h_2$ of the container 406 may be between about 17 cm and about 22 cm, with about 19.6 cm being a currently preferred height. An upper portion 406*b* of container 406 may be cylindrical in shape, with a height $h_3$, the difference between the overall height $h_2$ and the height $h_1$ of the tapered lower portion 406*a* of container 406. The diameter d of the upper portion 406*b* of container 406 may be between about 17 cm and about 22 cm, with about 19.8 cm being currently preferred. The size and dimensions of the fluidized bed can be changed to accommodate larger or smaller sample sizes.

A soil sample 405 may be disposed in the container 406. For example, a 15-gram soil sample 405 may occupy container 406 to a height $h_s$ of about 3.6 cm. Thus, with a 15-gram soil sample 405, there is a large disentrainment section 403 within the fluidized bed 410. The relatively large diameter d of the cylindrical upper portion 406*b* of container 406 enables a superficial velocity of the suspended matter to be reduced. Thus, disentrainment of particulate material will occur, and carry-over of unwanted material will be minimized. Asbestos may remain suspended and pass through outlet 409 to the collection filter 120.

The sizes of container 406 should not be construed as limiting the scope of the present invention, but merely as providing specifics of some exemplary embodiments. The container 406 may be much larger and configured to receive a larger quantity of soil therein. The soil separator system 100 may thus be useful for soil remediation, removing unwanted asbestos and other fine particulate contaminants from soil. The recovery fraction of asbestos using the soil separator system 100 of the present invention may be greater than the recovery fraction obtained using conventional methods.

The container 406 may include a removable lid 415 to facilitate placement of a soil sample 405 within container 406. The lid 415 may be flat or domed in shape and attached to the upper portion 406*b* of the container 406. The lid 415 may be attached with a threaded fitting, an interference fit, or any other suitable attachment method. A gasket or other seal element may optionally be used to provide a seal against air leakage between removable lid 415 and upper portion 406*b*. A vacuum line 455 may be removably attached to the lid 415 at the outlet 409 of container 406, or the vacuum line 455 may be permanently attached or integrally formed with the lid 415. The size of the vacuum line 455 may vary depending on the size of the container 406. One embodiment of the present invention includes a vacuum line 455 with a diameter of between about 5 mm and about 8 mm. The vacuum line 455 may be sealed with an outlet cap 457 (outlet caps 457 depicted as unsealed in FIG. 3 for clarity) when the vacuum line 455 is not in communication with the collection filter 120. Alternatively, the vacuum line 455 may be removable at the outlet 409 of container 406, and the outlet cap 457 may be placed thereon. An inlet cap 407 may be used to cover the inlet 401 of container 406 when the vacuum line 455 is not being applied across the fluidized bed 410 (inlet cap 407 is depicted as separate from inlet 401 for clarity). Alternatively, the inlet 401 and the outlet 409 may be sealed by disposing plugs (not shown) within the inlet 401 and the outlet 409.

The inlet cap 407 and the outlet cap 457 may be useful to retain the soil sample 405 within the container 406, for example, if the soil sample 405 will be transported before extracting the particulate matter, or for safe disposal of the container 406 and soil sample 405. An optional U-trap 102 (FIG. 1) may be added to the inlet of conical section 406a to prevent the soil sample from draining out of container 406.

The collection filter 120 may comprise, for example, a mixed cellulose ester filter with a 0.45 micron pore size as is used for the National Institute for Occupational Safety and Health Method No. 7400 for collecting asbestos samples from air. Filters for sampling asbestos typically have a pore size of about 0.45 micron. One suitable filter is available from the Millipore Corporation of Billerica, MA. The collection filter 120 may be examined, for example, in an off-site laboratory, to determine the type and concentration of particles trapped on the filter media. The asbestos content of a soil sample 105, 405 may thus be determined.

Although the foregoing description contains many specifics, these should not be construed as limiting the scope of the present invention, but merely as providing illustrations of some exemplary embodiments. Similarly, other embodiments of the invention may be devised that do not depart from the spirit or scope of the present invention. Features from different embodiments may be employed in combination. The scope of the invention is, therefore, indicated and limited only by the appended claims and their legal equivalents, rather than by the foregoing description. All additions, deletions, and modifications to the invention, as disclosed herein, which fall within the meaning and scope of the claims are to be embraced thereby.

What is claimed is:

1. A method of separating particulate matter from a soil sample, comprising:
    introducing the soil sample to a container;
    applying a vacuum to the container to draw a gas into the container;
    fluidizing particulates of the soil sample within the container using flow of the drawn gas;
    drawing gas containing at least some of the fluidized particulates from the container across a filter; and
    collecting the at least some of the fluidized particulates on the filter.

2. The method of claim 1, wherein introducing the soil sample to a container comprises introducing the soil sample to a funnel-shaped container.

3. The method of claim 1, further comprising disentraining a portion of the fluidized particulates to cause the disentrained portion of the fluidized particulates to remain within the container.

4. The method of claim 3, wherein disentraining a portion of the fluidized particulates comprises creating a cyclonic gas flow path in the container.

5. The method of claim 3, wherein disentraining a portion of the fluidized particulates comprises using at least one baffle in the container.

6. The method of claim 1, further comprising exhausting the drawn gas through a high-efficiency particulate-arresting (HEPA) filter.

7. A method of separating particulate matter from a soil sample, comprising:
    introducing the soil sample to a container;
    applying a vacuum to the container to draw a gas into the container;
    flowing the drawn gas through unfluidized particles of the soil sample;
    drawing gas containing at least some fluidized particles of the soil sample particulate matter from the container across a filter; and
    collecting the at least some of the fluidized particles of the soil sample particulate matter on the filter.

8. The method of claim 7, further comprising exhausting the drawn gas through a high-efficiency particulate-arresting (HEPA) filter.

9. A method of separating particulate matter from a soil sample, comprising:
    introducing the soil sample to a container;
    applying a vacuum to the container to draw a gas into the container;
    flowing the drawn gas above unfluidized particles of the soil sample;
    drawing gas containing at least some fluidized particles of the soil sample particulate matter from the container across a filter; and
    collecting the at least some of the fluidized particles of the soil sample particulate matter on the filter.

10. The method of claim 9, further comprising exhausting the drawn gas through a high-efficiency particulate-arresting (HEPA) filter.

* * * * *